US00PP32875P2

(12) United States Plant Patent
Radler

(10) Patent No.: US PP32,875 P2
(45) Date of Patent: Mar. 9, 2021

(54) FLORIBUNDA ROSE PLANT NAMED 'RADAPSHIN'

(50) Latin Name: *Rosa hybrida*
Varietal Denomination: Radapshin

(71) Applicant: The Conard-Pyle Company, West Grove, PA (US)

(72) Inventor: William Radler, Greenfield, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/602,836

(22) Filed: Dec. 12, 2019

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141, 145, 146, 147
CPC ..... A01H 5/0222
See application file for complete search history.

(56) References Cited

U.S. PATENT DOCUMENTS

PP11,691 P 12/2000 Zary
PP22,587 P2 3/2012 Harkness et al.

OTHER PUBLICATIONS https://issuu.com/starrosesandplants/docs/2020_starrosesandplants_catalog; Feb. 18, 2019; 1 page.*

* cited by examiner

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of Floribunda rose plant, herein referred to by its cultivar name, 'Radapshin', is provided which forms abundantly on a substantially continuous basis attractive, cup-like shaped yellow and orange colored blossoms. Attractive glossy, dark green foliage is formed, which contrasts beautifully with the blossoms. The growth habit is very bushy and upright. The new variety is well suited for providing attractive ornamentation in the landscape.

1 Drawing Sheet

Botanical/commercial classification:
Latin name: *Rosa hybrida.*
Varietal denomination: 'Radapshin'.

SUMMARY OF THE INVENTION

The new variety of *Rosa hybrida* Floribunda rose plant was created during June of 2006 in Milwaukee, Wis., U.S.A., by artificial pollination wherein two parents were crossed which previously had been studied in the hope that they would contribute the desired characteristics. The female parent (i.e., the seed parent) was the 'JACnepal' variety (U.S. Plant Pat. No. 11,691). The male parent (i.e., the pollen parent) was an unnamed breeder seedling (not patented).

The parentage of the new variety can be summarized as follows:

'JACnepal' x unnamed breeder seedling

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms attractive, cup-like shaped, yellow and orange colored blossoms,
(b) displays a very bushy and upright growth habit,
(c) forms vigorous vegetation, and
(d) provides attractive ornamental glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'JACnepal' variety (i.e., the seed parent) displays more petals, larger flowers, and weaker fragrance compared to the new variety. In addition, the unnamed breeding seedling male parent (i.e., the pollen parent) displays smaller flowers with more petals and is less compact compared to the new variety. Moreover, the new variety can be readily distinguished from other similar non-parental varieties. For example, the 'HARpageant' variety (U.S. Plant Pat. No. 22,587) displays flowers with more petals and a less upright growth habit compared to the new variety.

The new variety has been found to undergo asexual propagation at Wasco, Calif. and at Cochranville, Pa. by a number of routes, including vegetative cuttings. Asexual propagation by vegetative cuttings at Wasco, Calif. and at Cochranville, Pa. has shown that the characteristics of the new variety are stable and are strictly transmissible by such asexual propagation from one generation to another. Accordingly, the new variety undergoes asexual propagation in a true-to-type manner.

The new variety has been named 'Radapshin'.

The first offer for sale of the new variety was on Jan. 9, 2019 in Baltimore, Md., U.S.A. by the inventor or by another who obtained the new variety directly or indirectly from the inventor.

BRIEF DESCRIPTION OF THE PHOTOGRAPH

The accompanying photograph shows as nearly true as it is reasonably possible to make the same, in a color illustration of this character, a typical specimen of the new variety. The rose plant of the new variety was approximately three years of age and was observed during May 2019 while growing on its own roots and growing outdoors in a three-gallon container at Cochranville, Pa., U.S.A.

The drawing sheet—illustrates a specimen a plant with open blossoms.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of three-year-old specimens of the new variety during May while growing on their own roots in a three-gallon container at Cochranville, Pa., U.S.A.

Commercial classification: Floribunda Rose Plant.

Plant:

*Habit*.—Very bushy and upright.

*Height*.—Approximately 60.0 cm on average from the top of the soil plane.

*Width*.—Approximately 40.0 cm on average.

*Rooted plant*.—Approximately 6-8 weeks to produce.

*Marketable plant*.—Approximately 15 months to produce in a three gallon container.

Branches:

*Color*.—Young stems: commonly near Yellow-Green Group 144A. — old wood: commonly near Yellow-Green Group 146C.

*Length*.—Main stems: approximately 60.0 cm on average. — secondary stems: approximately 15.0 cm on average.

*Diameter*.—Main stems: approximately 6.0 mm on average. — secondary stems: approximately 3.0 mm on average.

*Texture*.—Thorny.

*Internode length*.—Approximately 4.0 cm on average.

*Thorns*.—Young thorns: length is approximately 7.0 mm on average, width is approximately 3.0 mm on average at point of attachment, and color is commonly near Greyed-Yellow Group 162B. — old thorns: length is approximately 1.2 cm on average, width is approximately 7.0 mm on average at point of attachment, and color is commonly near Greyed-Orange Group 164C. — number: typically 6 per internode. — shape: triangular with two flattened sides.

Foliage:

*General appearance*.—Dark green with a glossy aspect.

*Young foliage*.—Upper surface color: commonly near Yellow-Green Group 146A blended with near Greyed-Purple Group 183C with venation of near Greyed-Purple Group 183B. — under surface color: commonly near Greyed-Purple Group 183C blended with near Yellow-Green Group 146A with venation of near Greyed-Purple Group 183B.

*Old foliage*.—Upper surface color: commonly near Green Group 137A with indistinguishable venation. — under surface color: commonly near Green Group 137C with indistinguishable venation except the midrib which is near Red Group 51C.

*Petiole*.—Upper surface: color is commonly near Yellow-Green Group 144A with near Red Group 51B in the central portion and texture is smooth. — under surface: color is commonly near Yellow-Green Group 144A with overlay of near Greyed-Red Group 181D and texture is glandular with small thorns measuring approximately 2.0 mm on average. — length: approximately 4.0 cm on average. — diameter: approximately 2.0 mm on average.

*Rachis*.—Color of upper surface: commonly near Yellow-Green Group 144A. — color of under surface: commonly near Yellow-Green Group 144C. — length: approximately 8.0 mm on average. — diameter: approximately 2.0 mm on average. — texture of upper surface: glabrous. — texture of lower surface: glabrous, with a few small prickles.

*Stipules*.—Margin: entire to erose. — length: approximately 3.0 cm on average. — width: approximately 1.0 cm on average. — color of upper surface: commonly near Green Group 141B with near Greyed-Red Group 181C along the central rib. — color of lower surface: commonly near Green Group 141C. — number: a pair at the base where each leaflet attaches to the stem. — shape: linear. — apex: acute. — base: truncate. — texture: glabrous.

*5-leaflet leaf*.—Length: approximately 12.0 cm on average. — width: approximately 7.0 cm on average.

Leaflets:

*Number of leaflets*.—3, 5, and 7.

*Shape*.—Ovate; apex is rounded to moderately acute; and base is rounded.

*Texture*.—Upper and under surfaces is smooth.

*Margin*.—Serrate.

*Undulation*.—Weak.

*Terminal leaflet*.—Length: approximately 4.2 cm on average. — width: approximately 3.5 cm on average.

*Lower leaflet*.—Length: approximately 2.5 cm on average. — width: approximately 2.0 cm on average.

*Venation pattern*.—Reticulate.

Inflorescence:

*Number of flowers*.—Generally about 6 blooms on average on a plant at once.

*Number of blooms per stem*.—Typically 1 bloom per stem on average.

*Peduncle*.—Length: approximately 6.0 cm on average. — diameter: approximately 3.0 mm on average. — surface texture: sparely covered in short, flexible thorns that measure less than 1.0 mm in length. — color: commonly near Yellow-Green Group 144B.

*Sepals*.—Number: commonly 5. — length: approximately 3.0 cm on average. — width: approximately 1.0 cm on average. — margin: entire with extensions on two or three sepals measuring approximately 5.0 mm in length on average and 1.0 mm in width on average. — upper surface color and texture: commonly near Yellow-Green Group 144A; covered in short pubescence. — under surface color and texture: commonly near Yellow-Green Group 144B; puberulent. — shape: triangular. — apex: acute to aristate. — base: truncate as it joins the receptacle.

*Bud*.—Shape: ovoid. — length: approximately 2.0 cm on average. — width: approximately 1.5 cm on average. — color when opening: commonly near Orange-Red Group 31A.

*Flower*.—Diameter: approximately 10.0 cm on average. — height: approximately 4.0 cm on average. — duration: flower is on the plant approximately 7 days. — shape: cuplike. — form: double. — profile: flat to slightly convex. — number of petals under normal conditions: approximately 18 petals on average. — shape of the petal: — overall: broadly obovate. — apex: rounded. — base: cuneate. — petal length: approximately 5.0 cm on average. — petal width: approximately 4.5 cm on average. — petal margin: entire and strongly undulating. — petal texture of both surfaces: glabrous. — petal drop: excellent but with stamens and pistils persistent. — petaloids: none present. — fragrance: very slight sweet scent. — petal color when first and fully open: — upper surface of inner petals: commonly near Yellow-Orange Group 16D transitioning to Yellow-Orange Group 23D towards the petal apex. — under surface of inner petals: commonly near Yellow-Orange Group 16D. — upper surface of outer petals: commonly near Yellow-Orange Group 14C transitioning to Red Group 37C towards the petal apex. — under surface of outer petals: commonly near Yellow-Orange Group 16D transitioning to Red Group 37D towards the petal apex. — petal color at end of blooming: — upper surface: commonly near Red Group 36B with a basal spot of near Yellow-Orange Group 18D. — under surface: commonly near Red Group 36D with a basal spot of near Yellow-Orange Group 18D.

*Receptacle*.—Achenes stand on the bottom and wall. — color: commonly near Yellow-Green Group 144A. — diameter: approximately 1.0 cm on average. — depth: approximately 1.0 cm on average. — surface texture: smooth. — shape: round.

*Stamen*.—Number is approximately 100 on average. — anthers: number is approximately 100 on average; color is commonly near Yellow-Orange Group 17A; length is approximately 1.0 mm on average; and shape is oval. — filaments: length is approximately 9.0 mm on average and color is commonly near Yellow-Orange Group 17C.

*Pistils*.—Arrangement is separate and free; number is approximately 55 on average. — styles: length is approximately 2.0 mm on average and color is commonly near Orange-Red Group 30C. — stigmas: diameter is typically less than 1.0 mm and color is commonly near Yellow-Orange Group 14A.

*Pollen*.—Color is commonly near Yellow-Orange Group 20A and an abundant amount is present.

*Hips*.—None observed.

Development:

*Vegetation*.—Glossy, dark green, vigorous and strong.

*Blooming*.—Abundant and substantially continuous from May to November in Southeastern Pennsylvania.

*Resistance to disease*.—Very good resistance for black spot (*Diplocarpon rosae*) and powdery mildew (*Sphaerotheca pannosa*).

*Resistance or susceptibility to pests*.—None observed to date.

*Hardiness*.—Hardy to USDA Zone 5.

The new 'Radapshin' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant characterized by the following combination of characteristics:

(a) forms attractive, cup-like shaped, yellow and orange colored blossoms, (b) displays a very bushy and upright growth habit, (c) forms vigorous vegetation, and (d) provides attractive ornamental glossy, dark green foliage;

substantially as herein shown and described.

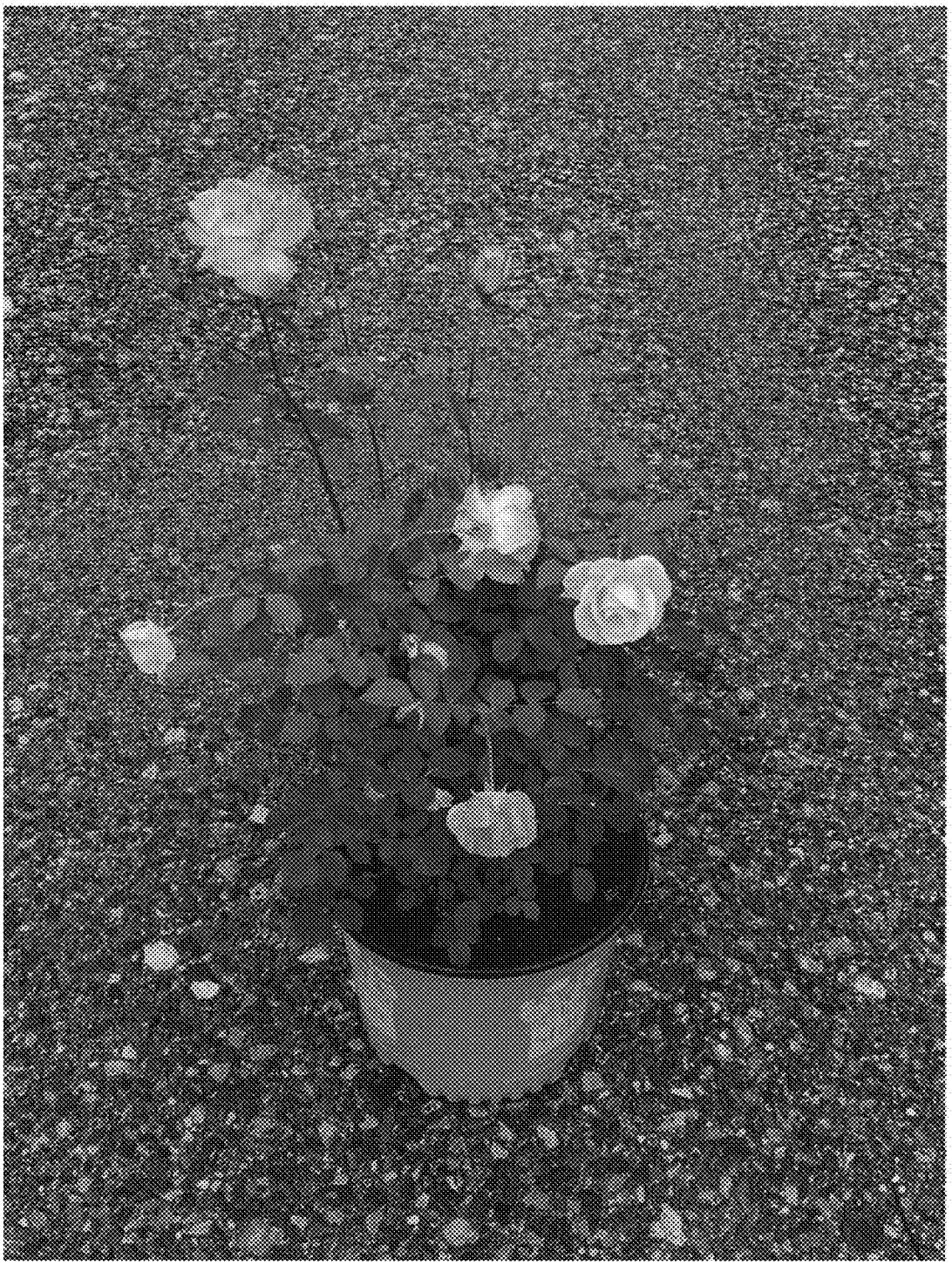

* * * * *